United States Patent [19]

Bossard et al.

[11] Patent Number: 5,101,159
[45] Date of Patent: Mar. 31, 1992

[54] ELECTROSTATIC PIN HOLE DETECTOR

[75] Inventors: Peter Bossard, Langhorne, Pa.; Jerry Kieres, Lockport, N.Y.

[73] Assignee: Trek, Inc., Medina, N.Y.

[21] Appl. No.: 525,761

[22] Filed: May 18, 1990

[51] Int. Cl.$^5$ .......................................... G01N 27/61
[52] U.S. Cl. .................................. 324/456; 324/452
[58] Field of Search ............... 324/452, 71.1, 454–458, 324/551, 554, 557, 558; 355/203, 210, 216

[56] References Cited

U.S. PATENT DOCUMENTS

| | | | |
|---|---|---|---|
| 3,851,229 | 11/1974 | Hayne et al. | 324/455 X |
| 4,233,562 | 11/1980 | Blythe | 324/452 X |
| 4,613,228 | 9/1986 | Sazuki et al. | 324/452 X |
| 4,760,342 | 7/1988 | Conrads et al. | 324/452 X |
| 4,780,680 | 10/1988 | Reuter et al. | 324/71.1 |

*Primary Examiner*—Jack B. Harvey
*Attorney, Agent, or Firm*—Hodgson, Russ, Andrews, Woods & Goodyear

[57] ABSTRACT

A surface capable of holding electrical charge wherein at least one sensing electrode having an edge is located in close physical proximity to the surface and is disposed so that upon relative movement between the surface and sensing electrode, charge on the surface crosses the edge of the electrode. The sensing electrode has a surface area facing the surface which is sufficiently small so as to minimize electrical noise when the electrode is in close proximity to the surface. Electrical charge is applied to the surface and relative movement is provided between the surface and sensing electrode while maintaining a constant distance therebetween. A current signal is induced in the sensing electrode in response to a variation in the surface charge crossing the edge of the electrode, and the signal is detected and electrical parameters thereof are measured to provide information on the charge density of the surface to determine the physical uniformity of the surface. Preferably a plurality of sensing electrodes are provided in a path extending along the surface in a direction generally cross-wise of the direction of relative movement between the surface and the sensing electrodes, and the detected current signals from the electrodes are scanned and then measured to obtain the aforesaid information. As a result, the size, number, and location of surface defects are readily determined.

20 Claims, 3 Drawing Sheets

ELECTROSTATIC PIN HOLE DETECTOR

BACKGROUND TO THE INVENTION

This invention relates to the electrostatic measurement art, and more particularly to a new and improved method and apparatus for determining the physical uniformity of a surface capable of being electrically charged.

One area of use of the present invention is in determining the surface quality and uniformity of photoconductive drums used in photocopiers, although the principles of the present invention can be variously applied to inspecting any surface capable of holding electrical charge. Heretofore, photoconducting drums have been inspected visually or by light scattering techniques to determine the presence of surface defects such as holes. These methods, however, are indirect in that they provide no measure of charge properties of the drum surface and they provide information only about the reflective properties of the surface.

It would, therefore, be highly desirable to provide a method and apparatus for quickly and reliably determining the physical quality and uniformity of a charged surface in a manner providing a measure of the charge properties of the surface. In providing such method and apparatus, important considerations involve minimizing electrical noise and maximizing resolution of detected signals. It would also be highly desirable to provide in such method and apparatus the capability of determining the size, number, and location of surface defects.

SUMMARY OF THE INVENTION

It is, therefore, a primary object of this invention to provide a new and improved method and apparatus for determining the physical uniformity of a surface capable of being electrically charged.

It is a further object of this invention to provide such a method and apparatus which rapidly and directly measures the charge density on the surface.

It is a further object of this invention to provide such a method and apparatus wherein detected electrical signals are of high resolution.

It is a further object of this invention to provide such a method and apparatus wherein electrical noise is minimized.

It is a further object of this invention to provide such a method and apparatus having the capability of determining the size, number and location of surface defects.

The present invention provides a method and apparatus for determining the physical uniformity of a surface capable of holding electrical charge wherein at least one sensing electrode having an edge is located in close physical proximity to the surface and is disposed so that upon relative movement between the surface and sensing electrode, charge on the surface crosses the edge of the electrode. The sensing electrode has a surface area facing the surface which is sufficiently small so as to minimize electrical noise when the electrode is in close proximity to the surface. Electrical charge is applied to the surface and relative movement is provided between the surface and sensing electrode while maintaining a constant distance therebetween. A current signal is induced in the sensing electrode in response to a variation in the surface charge crossing the edge of the electrode, and the signal is detected and electrical parameters thereof are measured to provide information on the charge density of the surface to determine the physical uniformity of the surface. Preferably a plurality of sensing electrodes are provided in a path extending along the surface in a direction generally cross-wise of the direction of relative movement between the surface and the sensing electrodes, and the detected current signals from the electrodes are scanned and then measured to obtain the aforesaid information. As a result, the size, number, and location of surface defects are readily determined.

The foregoing and additional advantages and characterizing features of the present invention will become clearly apparent a reading of the ensuing detailed description together with the included drawings wherein:

BRIEF DESCRIPTION OF THE DRAWING FIGURES

DETAILED DESCRIPTION OF THE ILLUSTRATED EMBODIMENT

Figure 1:
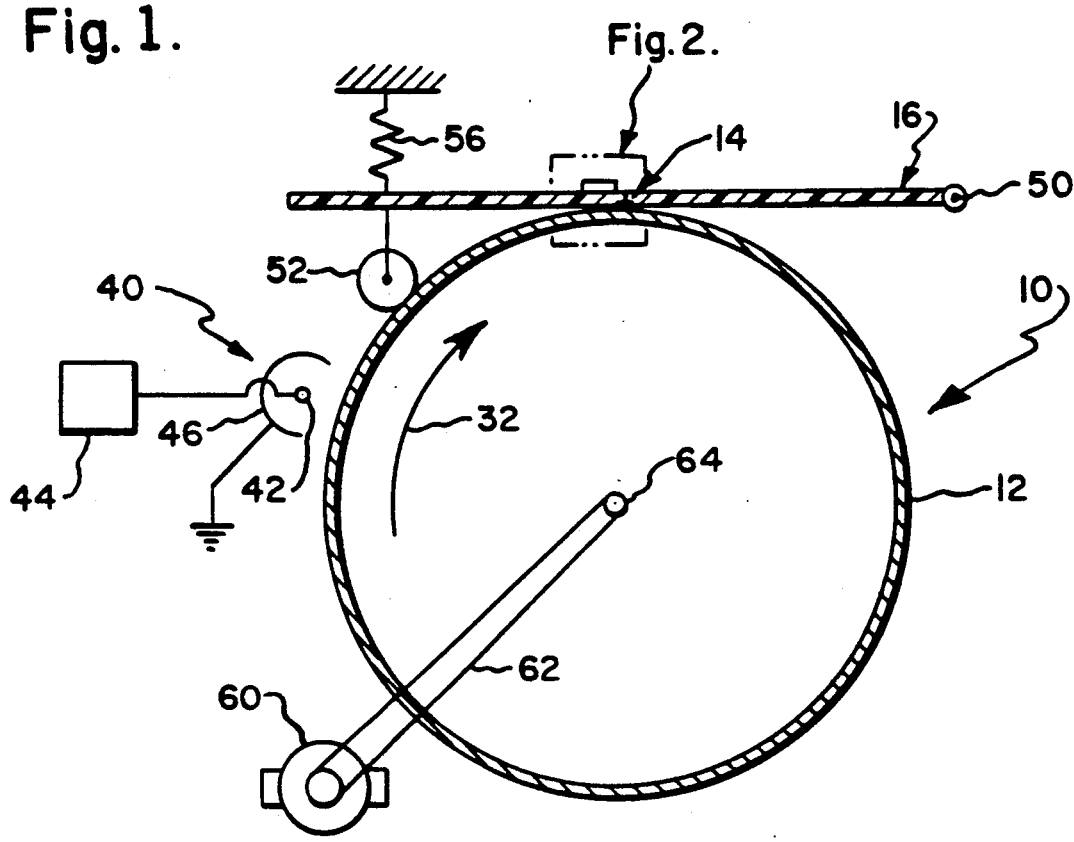
FIG. 1 is a schematic diagram illustrating the method and apparatus of the present invention.

FIG. 1 illustrates the method and apparatus according to the present invention for determining the physical uniformity, integrity, or homogeneity of a surface capable of holding electrical charge. A photoconductive drum 10 of the type employed in photocopiers is shown in cross-section and has an outer surface 12 which is to be inspected for defects such as holes. The apparatus according to the present invention comprises at least one sensing electrode generally designated 14 means generally designated 16 for locating electrode 14 in close proximity to surface 12. As shown more clearly in FIG. 2, electrode 14 according to the present invention has an edge 18 and is disposed so that upon relative movement between surface 12 electrode 14, electrical charge on surface 12 crosses edge 18 of electrode 14 in a manner which will be described in further detail presently.

The electrode supporting and locating means 16 is in the form of a printed circuit board rectangular in overall shape having a length commensurate with the axial length of drum 10 or corresponding dimension of any other surface being inspected, and having a width sufficient to accommodate circuit components on the side opposite electrode 14 as will be explained in further detail presently. Electrode 14 can be formed on the surface of board 16 by deposition, etching, or other suitable techniques well-known to those skilled in the art. In accordance with the present invention, electrode 14 has a surface area facing surface 12 which is sufficiently small so as to minimize electrical noise when electrode 14 is in close proximity to surface 12. In particular, electrode 14 is rectangular in shape wherein edge 18 extends lengthwise thereof and a second edge 20 extends parallel to edge 18 along the opposite side of electrode 14. Edges 18, 20 are joined by a pair of opposite edges, one of which is designated 22 in FIG. 2. By way of example, in an illustrative apparatus, electrode 14 is of tin-plated or gold-plated copper having a length of about 6 mm and a width of about 0.381 mm. Electrode 14 is connected by an electrical lead or conductor 28 to circuit components on the opposite side of load 16, one such component being designated 30 in FIG. 2.

Figure 3:
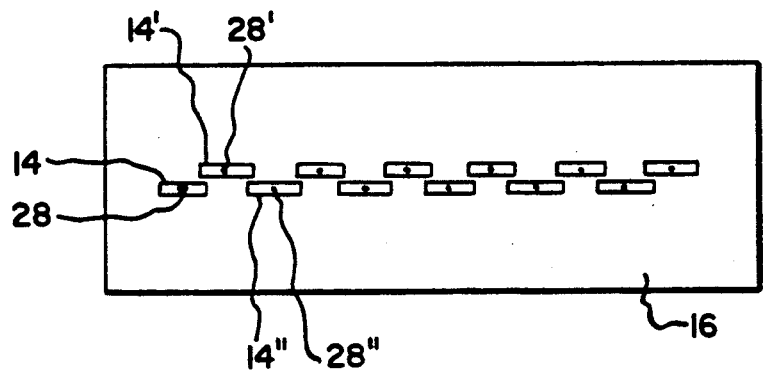
FIG. 3 is a schematic diagram illustrating the arrangement of sensing electrode in the apparatus of FIG. 1.

For inspecting most surfaces, the apparatus of the present invention includes a plurality of sensing electrodes each like electrode 14 arranged in a path extending in a direction generally cross-wise of the direction of relative movement between the electrodes and the surface. For example, in the arrangement illustrated in FIG. 1, the direction of rotation of drum 10 indicated by arrow 32 is in the plane of the paper, and therefore the plurality of sensing electrodes like electrode 14 extend along a path generally normal to the plane of the paper. FIG. 3 illustrates a typical arrangement of sensing electrodes on board 16 wherein, for example, 12 sensing electrodes are arranged along a path generally parallel to the longitudinal axis of board 16. This path extends cross-wise of the direction of relative movement between sensing electrodes and surface, i.e., in a direction parallel to the axis of rotation of drum 10 in the arrangement in FIG. 1. Three successively adjacent sensing electrodes are designated 14, 14', and 14", respectively. Alternate electrodes, i.e. 14 and 14" are in end-to-end alignment and the intermediate one, i.e. electrode 14' is slightly offset laterally and in slightly longitudinal overlapping relation with the corresponding ends of electrodes 14 and 14". This arrangement ensures that the entire portion of the surface will pass along the arrangement of electrodes and be sensed thereby. Each of the electrodes is connected to a corresponding lead or conductor, i.e. 28, 28', 28", to circuit components or the opposite side of board 16 which will be described in detail presently. While 12 sensing electrodes have been shown in the illustrative arrangement of FIG. 3, the total number is variable, depending upon the sizes of the various surfaces being measured, for example on the range of axial lengths of photoconductive drums being inspected.

The apparatus of the present invention further comprises means 40 for applying electrical charge to the surface being inspected. In the illustrative arrangement of FIG. 1 for inspecting surface 12 of the photoconductive drum 10, charging means 40 typically comprises a charging electrode in the form of a wire 42 extending longitudinally along and in closely spaced parallel relation to drum surface 12, a source of high DC voltage 44 connected electrically to wire 42 and a shield 46 located outwardly of wire 42 and surface 12 are typically connected electrically to ground.

In accordance with the present invention, a constant distance is maintained between sensing electrode 14 and surface 12 during relative movement therebetween. This can be accomplished by various suitable means, and in the arrangement of FIG. 1, board 16 is pivotally movable about point 50, a roller 52 rotatably mounted on board 16 contacts drum 10 and establishes a predetermined constant direction or spacing between the surface of the board 16 containing electrodes 14, and a biasing means 56 acts on board 16 urging roller 52 against drum 10. Various other mechanical arrangements can of course be employed.

There is also provided means for causing relative movement between surface 12 and sensing electrodes 14. In the arrangement shown, surface 12 is moved and to this end drum 10 is rotated by means including a drive motor 60 drivingly coupled through a pulley 62 to a shaft 64 upon which drum 10 is mounted for rotation. Various other mechanical drive arrangements can of course be employed. While in the present illustration surface 12 is moved relative to sensors 14, there may be other applications of the present invention wherein it may be feasible to move the sensors relative to the surface.

Figure 4:
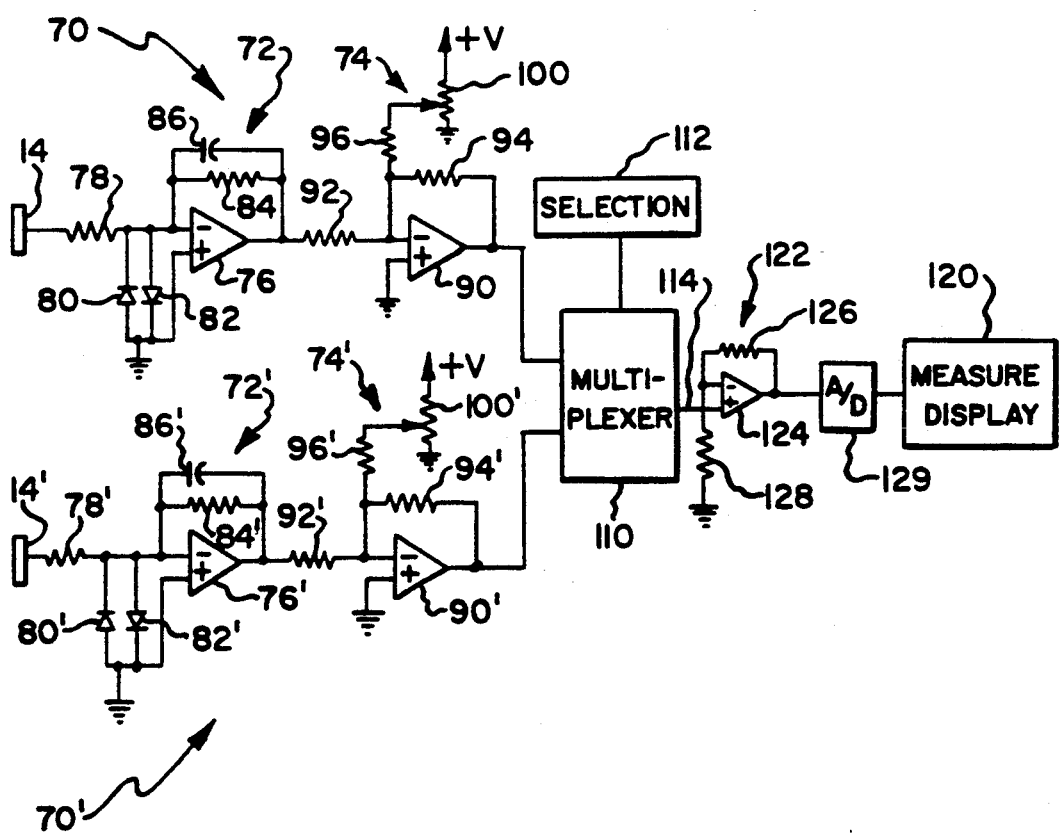
FIG. 4 is a schematic circuit diagram of the circuit for detecting current signals induced in the sensing electrodes.

Referring now to FIG. 4, the apparatus of the present invention further comprises circuit means generally designated 70 connected to the sensing electrodes 14 for detecting current signals induced in the electrodes in response to variations in the surface charge crossing the edges of the electrodes. In particular, circuit means 70 includes a current to voltage conversion or averaging stage 72 and an amplification stage 74, and there is provided a circuit means 70 for each sensing electrode 14. As shown in FIG. 4, conversion stage 72 includes a differential amplifier 76, the inverting input of which is connected through an input resistor 78 to sensing electrode 14. The non-inverting input of amplifier 76 is connected to an electrical ground or reference, and a pair of parallel, oppositely-poled diodes 80, 82 are connected across the amplifier inputs. The output of amplifier 76 is connected through the parallel combination of resistor 84 and capacitor 86 to the amplifier inverting input terminal. Amplification stage 74 includes a differential amplifier 90, the inverting input of which is connected through a resistor 92 to the output of amplifier 76 of the conversion stage. The non-inverting input of amplifier 90 is connected to an electrical ground or reference. The output of amplifier 90 is connected to one end of a voltage divider comprising the series combination of resistors 94 and 96. The other end of the voltage divider is connected to the wiper arm of a potentiometer 100 serving as an adjustable voltage source and connected between a source of positive DC voltage and ground. An intermediate point on the voltage divider, in particular the junction of resistors 94 and 96, is connected by line 104 to the inverting input terminal of amplifier 90.

As shown in FIG. 4, there is provided an identical circuit means for each sensing electrode, for example circuit means 70' for sensing electrode 14' and including identical components each designated by the same reference numerals provided with a prime superscript. Accordingly, for the illustrative arrangement previously described including 12 sensing electrodes, there would be provided 12 circuit means each identical to circuit means 70.

The apparatus of the present invention further includes scanning means generally designated 110 operatively connected to the circuit means for scanning the detected current signals. The scanning means 110 preferably comprises a multiplexer having an input connected to the output of circuit means 70, control or selection inputs connected to a source of control signals 112 and an output 114. In a typical arrangement including a large number of sensing electrodes, several multiplexers are provided, each one being associated with a group of sensing electrodes and corresponding circuit means in a manner which will be described.

The apparatus of the present invention also includes means generally designated 120 operatively connected to scanning means 110 for measuring at least one electrical parameter of the scanned signals to provide information on the charge density of surface 12 to determine the physical uniformity of surface 12. As shown in FIG. 4, the output of multiplexer 110 is connected through a buffer 122 to an input of measuring means 120. Buffer 122 comprises a differential amplifier 124, the non-inverting input of which is connected to the output of multiplexer 110. The output of amplifier 124 is connected through a resistor 126 to the inverting input which, in turn, is connected through a resistor 128 to an electrical ground. The output of buffer 122 is converted to the input of an analog-to-digital converter 129, the output of which is converted to measuring means which can comprise, for example, a video display or a computer. The former can provide a visual display of pulses having amplitudes indicative of variations in surface layer directly associated with surface defects in a manner which will be described. The latter can provide a histogram containing information as to size, location, and number of surface defects in a manner which will be described.

By way of example, in an illustrative apparatus including 48 sensing electrodes arranged in a manner like that of FIG. 3, there would be four scanning means 110 each associated with 12 sensing electrodes. Assuming consecutively numbered electrodes 14 extending along board 16, electrodes Nos. 1 through 4 would be associated with corresponding ones of the four scanning means 110, electrodes 5 through 8 would be associated corresponding ones of the scanning means 110, etc. By way of example, each scanning means is an AD8526A microprocessor. The circuit means 70 of electrodes Nos. 1 through 4 are connected to the S1 ports of the four microprocessors, the circuit means 70 of electrodes Nos. 5 through 8 are connected to the S2 ports thereof, etc. up to the S12 ports. The A0–A3 ports of the four microprocessors are connected together as are the $\overline{WR}$, EN and $\overline{RS}$ ports. The D port of each microprocessor is connected to the corresponding buffer.

In the foregoing illustrative arrangement, buffer amplifiers 124 are type AD712, differential amplifiers 90 and 76 are type OPA484KU, resistors 94 and 96 both have magnitudes of 10K, potentiometer 100 has a maximum voltage of about 15 volts, resistor 78 has a magnitude of 1k and resistor 84 has a magnitude of 10 Megohms.

Figure 2:
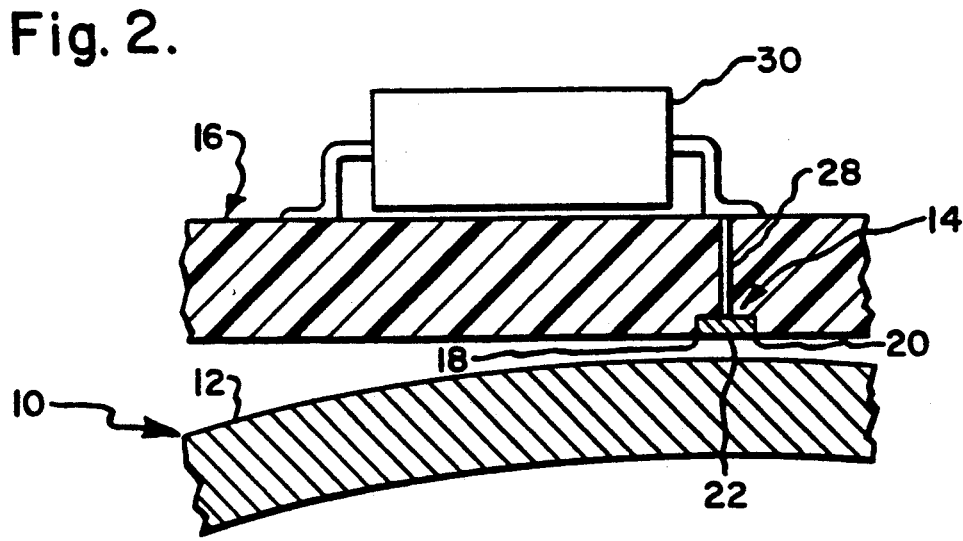
FIG. 2 is an enlarged schematic diagram of a portion of the apparatus of FIG. 1.

The apparatus of FIGS. 1 through 4 is operated to perform the method of the present invention in the following manner. Drum 10 is rotated by drive motor 60 and charging means 40 is operated to apply electrical charge to drum surface 12 in a known manner. Typically, about 390 volts DC is applied to drum 10. Charge is applied to the entire portion of surface 12 which is to be inspected or measured. Board 16 is moved to place sensing electrode 14 in close proximity to drum surface 12 as shown in FIGS. 1 and 2. Drum 10 is rotated clockwise as viewed in FIG. 1 so that the edge 18 of each sensing electrode is first exposed to charge as surface 12 passes relative to electrode 14.

The basic principle of the measurement relies on the relationship $q=CV$ where "q" is the charge coupled into a sensitive electrode 14 (sensor) from the surface 12 to be measured. "C" is the capacitive coupling to the surface and "V" is the voltage difference between the surface 12 and the sensor 14. Moving the surface 12 past the sensor 14 at a fixed distance gives $$i = CdV/dt$$

where "i" is the current in the sensor 14, "C" is the capacitive coupling between the surface 12 and the sensor 14 and "dV/dt" is the rate of change of the voltage on the surface 12.

The spacing between the detector 14 and the drum surface 12 should be constant and on the order of 100 microns or less. A defect moving past the detector 14 will induce a current in the detector because the charge crossing the edge 18 of the detector per unit time will vary, due to $i=C\ dV/dt$ where V is the voltage on the drum surface 12 and C is the capacitive coupling of the sensor 14. The noise picked up by each detector 14 having dimensions $0.381\ mm \times 6\ mm$ is relatively small because the area is only $2.286\ mm^2$. The signal is proportional to the speed at which the pin hole or defect crosses the edge 18 of the detector. In other words, since $i=cdV/dt=C(dV/dx)(dx/dt)$, the signal i is proportional to dx/dt, the speed at which the surface defect crosses edge 18 of sensing electrode 14. Maintaining the distance between the drum surface 12 and the detector 14 at a constant distance is important so that the signal i is proportional only to dV/dx and dx/dt.

As previously described, multiple sensors 14 are employed and digitally scanned in a drum sensor system. In a typical system there may be 12 to 128 sensors, more or less. The sensors 14 may be fabricated by known printed circuit techniques on one side of a circuit board 16 as previously described. The detection circuitry necessary for each sensor 14 can be placed on the other side of the printed circuit board 16. Each sensor 14 is the sensing element and input to the inverting mode of the circuit shown in FIG. 4. The geometry of each sensor electrode 14 is typically 0.4 mm by 6 mm as previously described. The long dimension is located perpendicular to the direction of motion of the drum 10 to provide sufficient room for the circuits on the opposite side of board 16.

As previously described, the basic signal is given by:
1) $i=C(dv/dt)$;
2) $i=C(dv/dx)(dx/dt)$; and
3) $q=CV$.

Putting the relationship $dV/dx=1/C(dq/dx)$ into equation 2) gives:

$$i=(dq/dx)(dx/dt)$$

This equation indicates that the signal is proportional to the charge variation, dq/dx, around the drum and the speed dx/dt that the charge variation dq/dt passes the detector.

The noise is generated by:

$$i_{noise}=C_N(dV/dt)$$

Where $C_N$ is the capacitance of the detector with respect to the noise source. $C_N$ is proportional to the area of the sensor. Capacitance is a geometrical quantity and given a fixed spacing becomes large when the area of the detector is increase. However, the signal remains the same, therefore minimizing the area of the detector will minimize the noise and maximize the signal to noise ratio.

The signal generated at the output of the circuit 70 shown in FIG. 4 is:

$$i = C_h dV/dt$$

where $C_h$ is the capacitance of the hole to the sensor. For 100 microns × 100 microns hole (defect) $C_h$ can be approximated as a parallel plate capacitor:

$$C_h = C_o A/d = 8.85 \times 10^{-12} (10^{-4})^2 / 7.62 \times 10^{-5}$$

$$C_h = 10^{-15} \text{ farads}$$

If $dV = 100$ volts and an 8 cm diameter drum is rotating at 2 revolutions per second, dt is $5 \times 10^{-5}$ seconds and $$i = (10^{-15} \text{ farads}) \, 100 \text{ Volts}/5 \times 10^{-5} \text{ sec} = 2 \times 10^{-9} \text{ amperes}$$

This magnitude of current is easily measured. If the area of the hole is reduced by a factor of 16 corresponding to a 25 u by 25 u defect, the current generated would be approximately 125 pA. These current levels can be measured easily at a rate of more than 100 k sample/sec. The readings from a typical drum form a matrix of numbers typically 48 by 15,000. This array of numbers contains the information necessary to locate all the effective pin holes or defects on a surface 250 mm × 280 mm or an equivalent area corresponding to the drum 10 having an axial length of 28 cm and a diameter of 8 cm. The size of the effective pin hole (defect) in this case is 50 u by 50 u and a $\Delta V = 50$ volts.

Figure 5:
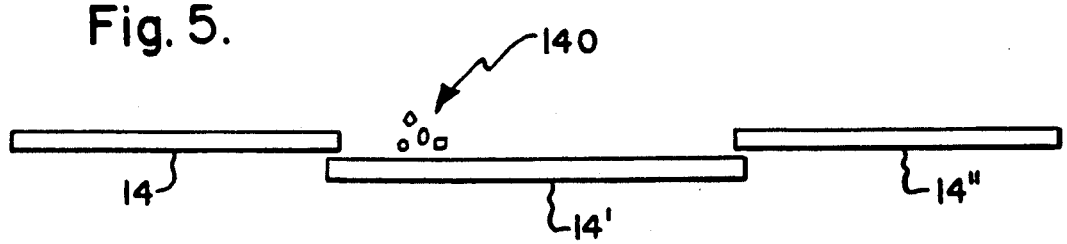
FIG. 5 is a schematic diagram illustrating the relationship between surface defects and the sensing electrodes.
Figure 6A:
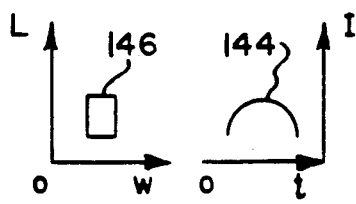
FIGS. 6A-6D are schematic diagrams including graphs containing waveforms illustrating the method and apparatus of the present invention.
Figure 6C:
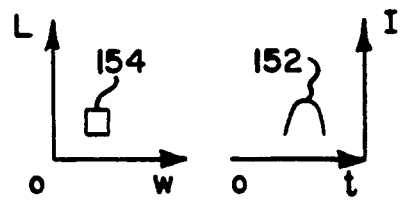
Figure 6B:
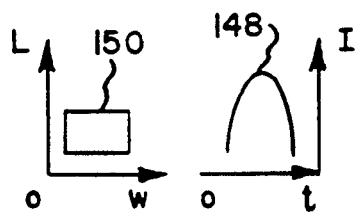
Figure 6D:
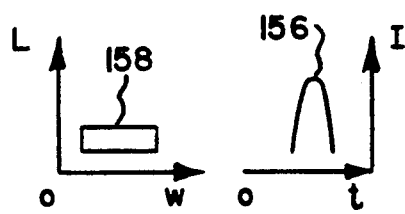

The method and apparatus of the present invention is illustrated by FIGS. 5 through 7 which show the types and behavior of signals induced in sensing electrodes 14 and ultimately displayed in apparatus such as that designated 120 in FIG. 4. FIG. 5 shows three sensing electrodes or detectors 14, 14', and 14" which typically are offset from each other as previously described with a group or pattern 140 of surface holes or defects about to infringe on the edge 18' of sensing electrode 14'. FIGS. 6a through 6d illustrate the type of signal that would be displayed in apparatus 120 when a hole or defect crosses the boundary or edge 18 of a sensing electrode 14. Each graph presents length (L) vs. width (W) of the defect and amplitude vs. time of the corresponding current signal. Thus, FIG. 6a illustrates the signal 144 resulting from a long rectangular hole 146, FIG. 6b shows the signal 148 resulting from a square hole 150, FIG. 6c depicts the signal 152 resulting from a small square hole 154, and FIG. 6d illustrates the signal 156 resulting from a short (in length) rectangular hole 158. The length of the hole, i.e. the vertical dimension as viewed in FIG. 6, determines the width of the resulting pulse. That is because the length of the hole is in the direction of relative movement between surface 12 and sensing electrode 14, i.e. the length of the hole is orthogonal to the electrode edge 18. The width of the hole, i.e. the horizontal dimension viewed in FIG. 6, determines the height or amplitude of the resulting pulse. That is because the current signal amplitude is determined by the amount of charge passing by the edge 18 of sensing electrode 14, i.e. dq/dt, and the wider the hole the more dq/dt passing edge 18.

Figure 7A:
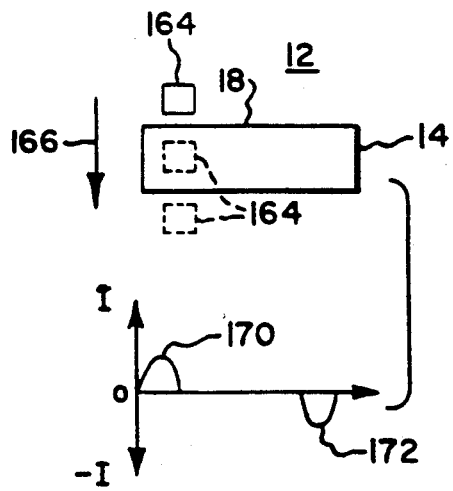
FIGS. 7A and 7B are schematic diagrams including graphs containing waveforms further illustrating the method and apparatus of the present invention.
Figure 7B:
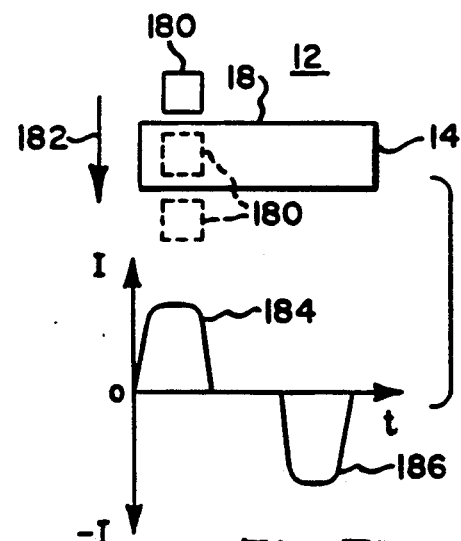

FIGS. 7a and 7b illustrate the time sequence of current signals generated when two different sized holes or defects pass by the sensing electrode. Referring to FIG. 7a, a square-shaped hole or defect 164 in surface 12 moves in the direction of arrow 166 toward edge 18 of sensing electrode 14. The first broken line representation of hole 164 is after it has entered entirely past edge 18 and is entirely in registry with electrode 14. The second broken line representation of hole 164 is after it has left or past by electrode 14. Waveform 170 is the current pulse generated as hole 164 enters the sensitive region of electrode 14 and passes edge 18, and waveform 172 is the current pulse generated as hole 164 leaves the region of electrode 14 passing the opposite edge. Waveform 170 is positive-going because as hole 164 passes edge 18 and enters the region of electrode 14, dq/dt relative to electrode 14 is negative. Waveform 172 is negative-going because as hole 164 passes the opposite edge and leaves the region of electrode 14, dq/dt relative to electrode 14 is negative. The time between the fall of pulse 170 and the rise of pulse 172 is a measure of the width of electrode 14 minus the length of defect 164, provided the width of detector 14 is greater than the length of defect 164 measured in the direction of relative movement between surface 12 and electrode 14.

Referring now to FIG. 7b, a square-shaped hole or defect 180, four times larger in area than defect 164, moves in the direction of arrow 182 toward edge 18 of sensing electrode 14. Waveform 184 is the current pulse generated as hole 180 enters the sensitive region of electrode 14 and passes edge 18, and waveform 186 is the current pulse generated as hole 180 leaves the region of electrode 14 passing the opposite edge. The amplitudes of pulses 184, 186 are larger than the amplitudes of pulses 170, 172 due to the fact that hole 180 is larger in area than hole 164. The widths or durations of pulses 184, 186 are larger than the widths or durations of pulses 170, 172 because the length of defect 180 is greater than the length of defect 164, the length being measured in the direction of relative movement between electrode 14 and surface 12. The time between the fall of pulse 184 and the rise of pulse 186 is a measure of the width of electrode 14 minus the length of defect 180, provided the width of detector 14 is greater than the length of defect 180 measured in the direction of relative movement between surface 12 and electrode 14. This parameter is shorter as compared to that for the sequence of FIG. 7a due to the fact that defect 180 is larger than defect 164.

In view of the foregoing, in order to obtain useful information about the surface holes or defects, the width of each sensing electrode, i.e. the dimension parallel to the direction of relative movement between surface 12 and electrode 14, should be greater than the maximum length of the hole or defects being measured.

The edge effect resulting from holes or defects crossing the edge 18 of each sensing electrode 14 provides current pulses with fast rising leading edges as shown in FIG. 7 thereby resulting in a detector having a high resolution. In fact, it has been determined that the detector arrangement in the foregoing configuration has a resolution about 240 times better around the circumference of drum 10 than along the axial length of drum 10.

Providing a plurality of sensing electrodes 114 along a path as previous described, each electrode having a relatively small surface area facing surface 12, results in a significant reduction in electrical noise as previously explained.

The current signals induced in sensing electrode 14 in response to surface holes or defects have several electrical parameters, as described in connection with FIG. 7, which can be inspected or measured to provide information as to the holes or defects. Pulse amplitude provides a measure of the hole size, in particular the width of the hole a mentioned in connection with FIG. 7. Pulse width also provides a measure of the hole size, in particular the length of the hole.

Current pulses induced in the sensing electrodes 14 in response to movement of surface 12 relative thereto can be arranged in a matrix as previously described by means of computer to form a histogram. The horizontal axis contains points corresponding to the location of each of the sensing electrodes along the one dimension of the surface being measured, i.e. the axial length of drum 10. The vertical axis contains points corresponding to the number of holes or defects sensed during travel of the electrode 14 along the other dimension of the surface, i.e. along the circumference of drum 10.

The method and apparatus of the present invention provide a rapid and reliable determination of the quality, i.e. physical uniformity, of a surface such as the surface of a photosensitive drum. The approach is direct, providing information of the charge properties of the surface. High resolution information signals are obtained and electrical noise is minimized.

It is therefore apparent that the present invention accomplishes its intended objects. While an embodiment of the present invention has been described in detail, that is for the purpose of illustration, not limitation.

We claim:

1. A method of determining the physical uniformity of a surface capable of holding electrical charge comprising the steps of:
   a) applying electrical charge to said surface;
   b) providing at least one sensor in close proximity to said surface and having an edge;
   c) disposing said sensor so that upon relative movement between said surface and said sensor charge on said surface crosses said edge of said sensor;
   d) causing relative movement between said surface and said sensor;
   e) detecting a current signal induced in said sensor in response to a variation in the surface charge crossing said edge of said sensor according to the relationship $i=C(dV/dx)(dx/dt)$ where i is the current in said sensor, C is the capacitive coupling between said surface and said sensor, $dV/dx$ is the change in voltage along said surface and $dx/dt$ is the speed at which said surface charge variation crosses said edge of said sensor;
   f) measuring an electrical parameter of the current signal to provide information on the charge density of said surface to determine the uniformity of said surface, said edge of said sensor being positioned sufficiently close to said surface so that the current signal has sufficient amplitude and response time for detection of non-uniformities in said surface.

2. A method according to claim 1, further including selecting the area of said sensor to be sufficiently small so as to minimize electrical noise when said sensor is in close proximity to said surface.

3. A method according to claim 1, further including providing a plurality of sensors arranged in a path extending along said surface in a direction generally crosswise of the direction of relative movement between said sensors and said surface.

4. A method according to claim 3, further including selecting the area of each of said sensors to be sufficiently small so as to minimize electrical noise when said sensors are in close proximity to said surface.

5. A method according to claim 3, further including scanning the detected current signals in said sensors to provide information on the portion of said surface corresponding to the extent of said path.

6. A method according to claim 1, further including the step of maintaining a constant distance between said sensor and said surface during said relative movement therebetween so that the current i in said sensor is proportional only to $dV/dx$ and $dx/dt$.

7. A method according to claim 1, wherein said surface comprises the outer surface of a photoconductive drum and wherein said step of causing relative movement comprises rotating said drum about the longitudinal axis thereof.

8. A method of determining the physical uniformity of a surface capable of holding electrical charge comprising the steps of:
   a) applying electrical charge to said surface;
   b) providing a plurality of sensors in close proximity to said surface and in a path extending along said surface, each of said sensors having an edge;
   c) disposing said sensors so that upon relative movement between said surface and said sensors charge on said surface crosses an edge of a sensor;
   d) selecting the area of each of said sensors to be sufficiently small so as to minimize electrical noise when said sensors are in close proximity to said surface;
   e) causing relative movement between said surface and said sensors so that the direction of movement of said surface is generally orthogonal to said path containing said sensors;
   f) detecting current signals induced in said sensors in response to a variation in the surface charge crossing said edges of said sensors according to the relationship $i=C(dV/dx)(dx/dt)$ where i is the current in said sensors, C is the capacitive coupling between said surface and said sensors, $dV/dx$ is the change in voltage along said surface and $dx/dt$ is the speed at which surface charge variation crosses said edges of said sensors;
   g) scanning the detected current signals; and
   h) measuring an electrical parameter of the scanned signals to provide information on the charge density of said surface to determine the uniformity of said surface, said edges of said sensors being positioned sufficiently close to said surface so that the current signals have sufficient amplitude and response time for detection of non-uniformities in said surface.

9. A method according to claim 8, further including the step of maintaining a constant distance between said sensors and said surface during said relative movement therebetween so that the current i in said sensors is proportional only to $dV/dx$ and $dx/dt$.

10. A method according to claim 8, wherein said surface comprises the outer surface of a photoconductive drum and wherein said step of causing relative movement comprises rotating said drum about the longitudinal axis thereof.

11. Apparatus for inspecting a surface to determine the physical uniformity thereof wherein said surface is capable of holding electrical charge, said apparatus comprising:
   a) at least one sensing electrode having an edge;

b) means for locating said sensing electrode in close proximity to said surface and for disposing said electrode so that upon relative movement between said surface and said sensing electrode charge on said surface crosses said edge of said electrode;

c) means for applying electrical charge to said surface;

d) means for causing relative movement between said surface and said sensing electrode;

e) circuit means connected to said sensing electrode for detecting a current signal induced in said electrode in response to variation in the surface charge crossing said edge of said electrode according to the relationship $i = C(dv/dx)(dx/dt)$ where i is the current in said sensing electrode, C is the capacitive coupling between said surface and said sensing electrode, $dV/dx$ is the change in voltage along said surface and $dx/dt$ is the speed at which said surface charge variation crosses said edge of said sensing electrode; and f) means operatively connected to said circuit means for measuring an electrical parameter of said current signal to provide information on the charge density of said surface to determine the uniformity of said surface, said edge of said sensing electrode being positioned sufficiently close to said surface so that the current signal has sufficient amplitude and response time for detection of non-uniformities in said surface.

12. Apparatus according to claim 11, wherein said electrode has a surface area facing said surface which is sufficiently small so as to minimize electrical noise when said electrode is in close proximity to said surface.

13. Apparatus according to claim 11, further including a plurality of sensing electrodes arranged in a path extending along said surface in a direction generally cross-wise of the direction of relative movement between said electrodes and said surface.

14. Apparatus according to claim 13, wherein each of said electrodes has a surface area facing said surface which is sufficiently small so as to minimize electrical noise when said electrode is in close proximity to said surface.

15. Apparatus according to claim 13, further including scanning means operatively connected to said circuit means and to said measuring means for scanning the detected current signals in said electrodes to provide information on the portion of said surface corresponding to the extent of said path.

16. Apparatus according to claim 11, further including means for maintaining a constant distance between said electrode and said surface during relative movement therebetween so that the current i in said sensing electrode is proportional only to $dV/dx$ and $dx/dt$.

17. Apparatus according to claim 11, wherein said surface comprises the outer surface of a photoconductive drum and wherein said means for causing relative movement comprises motive means drivingly coupled to said drum for rotating said drum about the longitudinal axis thereof.

18. Apparatus for inspecting a surface to determine the physical uniformity thereof wherein said surface is capable of holding electrical charge, said apparatus comprising:

a) a plurality of sensing electrodes each having an edge;

b) means for locating said sensing electrodes in close proximity to said surface in a path extending along said surface and for disposing said sensing electrodes so that upon relative movement between said surface and said electrodes charge on said surface crosses said edges of said electrodes;

c) each of said sensing electrodes having a surface area facing said surface which is sufficiently small so as to minimize electrical noise when said electrodes are in close proximity to said surface;

d) means for applying electrical charge to said surface;

e) means for causing relative movement between said surface and said sensing electrodes in a manner such that the path in which said electrodes are located is in a direction generally cross-wise of the direction of relative movement between said surface and said sensing electrodes;

f) circuit means connected to said sensing electrodes for detecting current signals induced in said electrodes in response to variations in the surface charge crossing said edges of said electrodes according to the relationship $i = C(dV/dx)(dx/dt)$ where i is the current in said sensing electrodes, C is the capacitive coupling between said surface and said sensing electrodes, $dV/dx$ is the change in voltage along said surface and $dx/dt$ is the speed at which surface charge variation crosses said edges of said sensing electrode;

g) scanning means operatively connected to said circuit means for scanning the detected current signals; and h) means operatively connected to said scanning means for measuring an electrical parameter of the scanned signals to provide information on the charge density of said surface to determine the uniformity of said surface, said edges of said sensing electrodes being positioned sufficiently close to said surface so that the current signals have sufficient amplitude and response time for detection of non-uniformities in said surface.

19. Apparatus according to claim 18, further including means for maintaining a constant distance between said sensing electrodes and said surface during relative movement therebetween so that the current i in said sensing electrodes is proportional only to $dV/dx$ and $dx/dt$.

20. Apparatus according to claim 18, wherein said surface comprises the outer surface of a photoconductive drum and wherein said means for causing relative movement comprises motive means drivingly coupled to said drum for rotating said drum about the longitudinal axis thereof.

* * * * *